(12) United States Patent
Haidukewych

(10) Patent No.: US 7,270,655 B2
(45) Date of Patent: Sep. 18, 2007

(54) AUTOLOGOUS MATERIAL DELIVERY APPARATUS AND METHOD

(76) Inventor: George J. Haidukewych, 15301 Bursley, Tampa, FL (US) 33647

( * ) Notice: Subject to any disclaimer, the term of this patent is extended or adjusted under 35 U.S.C. 154(b) by 142 days.

(21) Appl. No.: 11/036,246

(22) Filed: Jan. 14, 2005

(65) Prior Publication Data

US 2006/0161093 A1    Jul. 20, 2006

(51) Int. Cl.
*A61M 31/00* (2006.01)
*A61F 5/00* (2006.01)

(52) U.S. Cl. .................................. 604/522; 606/86
(58) Field of Classification Search ............. 604/6.11, 604/522; 600/36; 606/86, 92–94
See application file for complete search history.

(56) References Cited

U.S. PATENT DOCUMENTS

| | | | |
|---|---|---|---|
| 5,199,942 A | 4/1993 | Gillis | |
| 5,270,300 A | 12/1993 | Hunziker | |
| 5,725,492 A * | 3/1998 | Igo et al. ................... | 604/6.11 |
| 5,853,746 A | 12/1998 | Hunziker | |
| 5,914,121 A | 6/1999 | Robey et al. | |
| 6,303,138 B1 | 10/2001 | Peterson et al. | |
| 6,325,806 B1 | 12/2001 | Fox | |
| 6,596,296 B1 | 7/2003 | Nelson et al. | |
| 6,623,733 B1 | 9/2003 | Hossainy et al. | |
| 6,667,034 B2 | 12/2003 | Palsson et al. | |
| 6,696,410 B1 | 2/2004 | Lee et al. | |
| 2002/0032444 A1 | 3/2002 | Mische | |
| 2002/0091077 A1 | 7/2002 | Rueger et al. | |
| 2002/0188240 A1 | 12/2002 | Gorsuch | |
| 2003/0103951 A1 | 6/2003 | Pittenger et al. | |
| 2003/0235561 A1 | 12/2003 | Vandenburgh et al. | |
| 2004/0009600 A1 | 1/2004 | Bowlin et al. | |
| 2005/0181977 A1 * | 8/2005 | Hunter et al. ................ | 514/2 |
| 2006/0074399 A1 * | 4/2006 | Bates ........................ | 604/522 |

* cited by examiner

*Primary Examiner*—Tatyana Zalukaeva
*Assistant Examiner*—Melanie J Hand
(74) *Attorney, Agent, or Firm*—David W. Pettis, Jr., P.A.

(57) ABSTRACT

An apparatus and method for providing autologous medical treatment to a patient. The apparatus is characterized by its provision of a harvest catheter operatively connected to a pump and a delivery catheter operatively connected to the pump downstream from the harvest catheter, whereby material from the patient's donor site may be delivered to the patient's treatment site. The method is characterized by surgically implanting at least a first end of the harvest catheter and at least a second end of the delivery catheter within the patient's body. The entire apparatus may be implanted within the patient.

4 Claims, 3 Drawing Sheets

AUTOLOGOUS MATERIAL DELIVERY APPARATUS AND METHOD

BACKGROUND OF THE INVENTION

1. Field of the Invention

The present invention relates to an apparatus and method for the autologous delivery of material such as, for example, tissue through the use of catheters and a pump. As is set forth in greater detail below, the apparatus may be inserted surgically within the patient, or portions of the apparatus may be external. The apparatus is also adaptable whereby medicaments, in addition to autologous material, may be delivered to the patient by the pump.

2. Description of the Prior Art

As an example of autologous material delivery, autologous bone grafting is a relatively common procedure in orthopedic surgery. Multiple fractures, fusions, infections, and nonunions are commonplace, and such conditions are typically treated with some form of autologous bone grafting. In a typical situation, bone graft material is obtained from the pelvis at the iliac crest, but can also be obtained from other skeletal sites such as, for example, the proximal tibia. Bone grafting does involve an additional incision for harvesting of the graft material, resulting in potential pain and donor site morbidity. Furthermore, this procedure is typically performed one time, where all of the bone graft material is removed, or the bone marrow is aspirated, and the autologous graft material is delivered in a single operation to the desired treatment site.

Numerous devices are described in the literature, both technical and patent, for more efficient removal, and such devices involve mechanical augers and other such devices for bone graft harvest.

Because the graft material is harvested in one step and then placed at a second site, current bone marrow aspirate technology and selective cell filtration involves large, multiple aspirate passes to obtain material, and this is often quite painful for the patient. One example of current, state-of-the-art systems and their use is provided in U.S. Pat. No. 6,325,806 to Fox. Another example is provided in U.S. Patent Application Publication No. US 2002/0188240 to Gorsuch.

Not withstanding the existence of current autologous collection and delivery systems, it is clear that there remains a great need for such a system that is capable of providing harvest material to a treatment site according to a system and method which may be surgically implanted in a single operation, while providing autologous material to a treatment site over a prolonged period of time in a controllable fashion.

SUMMARY OF THE INVENTION

The present invention relates to an autologous material delivery apparatus and method for providing medical treatment to a patient. The apparatus, in a preferred embodiment, comprises a harvest catheter having a first harvest end and a second harvest end, with the first harvest end being disposed in material receiving relation to a material donor site of the patient. A pump is provided having a harvest port and a delivery port in communication with and downstream from the harvest port. The harvest port is operatively connected to the second harvest end of the harvest catheter, so that the material from the material donor site may be drawn into the pump. A delivery catheter is provided having a first delivery end and a second delivery end. The first delivery end is operatively connected to the pump's delivery port, and the second delivery end of the delivery catheter is disposed in material delivering relation to the treatment site of the patient. Thus, autologous treatment may be provided by withdrawing material from the donor site by the action of the pump, and delivering the material to the treatment site, also by action of the pump. Also claimed is the method for providing autologous medical treatment to a patient using the apparatus of this invention.

The invention accordingly comprises the several steps and relation of one or more of such steps with respect to each of the others, and the apparatus embodying features of construction, combinations of elements, and arrangements of parts which are adapted to effect such steps, all as exemplified in the following detailed description, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

Similar reference characters refer to similar parts throughout the several views of the drawings.

DETAILED DESCRIPTION

The current invention relates to an apparatus and method for selective cannulation of a patient's donor site and delivery of the harvested material via a series of catheters and an intervening pump. Typically, the collected material is tissue used for trauma repair, such as bone tissue or marrow for ameliorating the repair of a broken bone, or for assisting in a spinal fusion procedure. Thus, harvested material is delivered selectively and over time to a treatment site.

Figure 1:
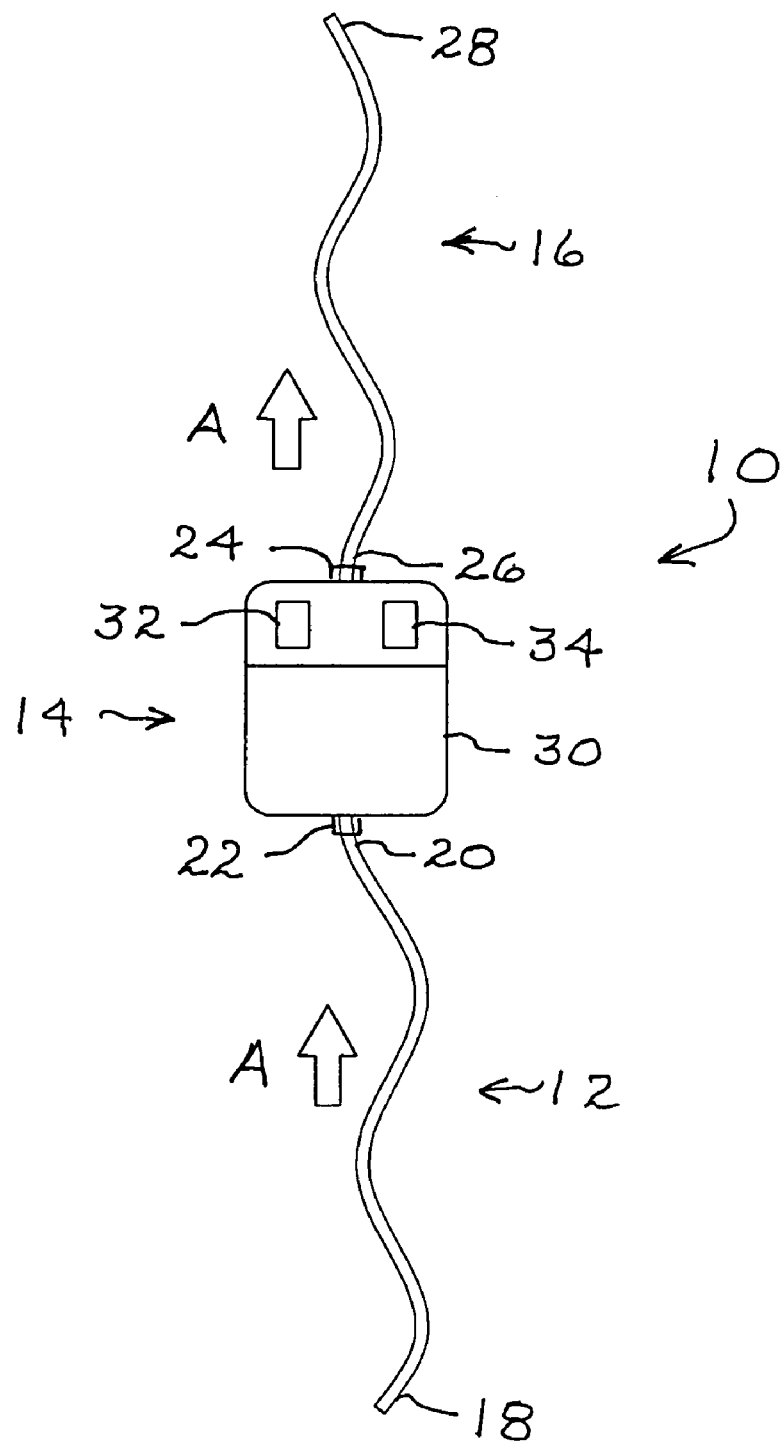
FIG. 1 is a schematic representation of the autologous material delivery apparatus of this invention.

Referring to the view of FIG. 1, the autologous material delivery apparatus is generally indicated as 10. As shown in the view of FIG. 1, apparatus 10 comprises a harvest catheter generally indicated as 12, a pump generally indicated as 14, and a delivery catheter generally indicated as 16. Harvest catheter 12 comprises a first harvest end 18 and a second harvest end 20. Pump 14 comprises a harvest port 22 and a delivery port 24 which is in fluid communication with and downstream from harvest port 22. Delivery catheter 16 comprises a first delivery end 26 and a second delivery end 28. In this preferred embodiment for the autologous material delivery apparatus 10, pump 14 is enclosed within pump housing 30, and further includes a flow rate controller 32 and a time rate controller 34. Directional arrows A illustrate the delivery of material from first harvest end 18, through pump 14, and to second delivery end 28, all as more fully described below.

Figure 2:
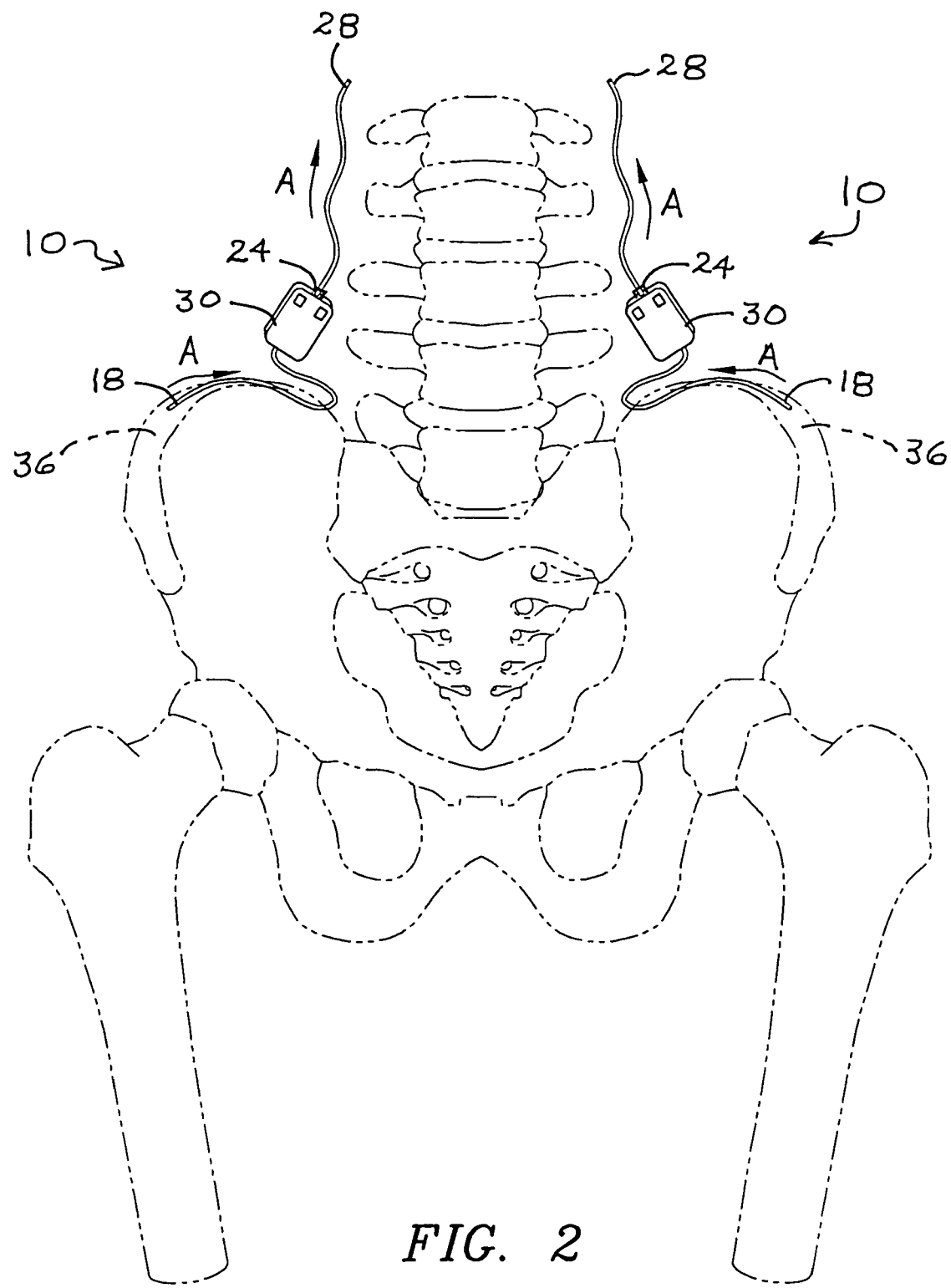
FIG. 2 represents placement of a pair of the autologous material delivery apparatus of this invention, with the patient's partial skeleton shown in phantom.

Turning to the view of FIG. 2, there is a representation of the use of a pair of the autologous material delivery apparatus 10 wherein the patient is undergoing a spinal fusion. First harvest end 18 of each of the harvest catheters 12 is surgically disposed to harvest material from the patient's iliac crest 36. From there, harvested material is passed by each of the pumps 14 to the respective second delivery ends 28 of delivery catheter 16, with the respective second delivery ends 28 surgically disposed adjacent the patient's treatment site for the spinal fusion (not shown).

Figure 3:
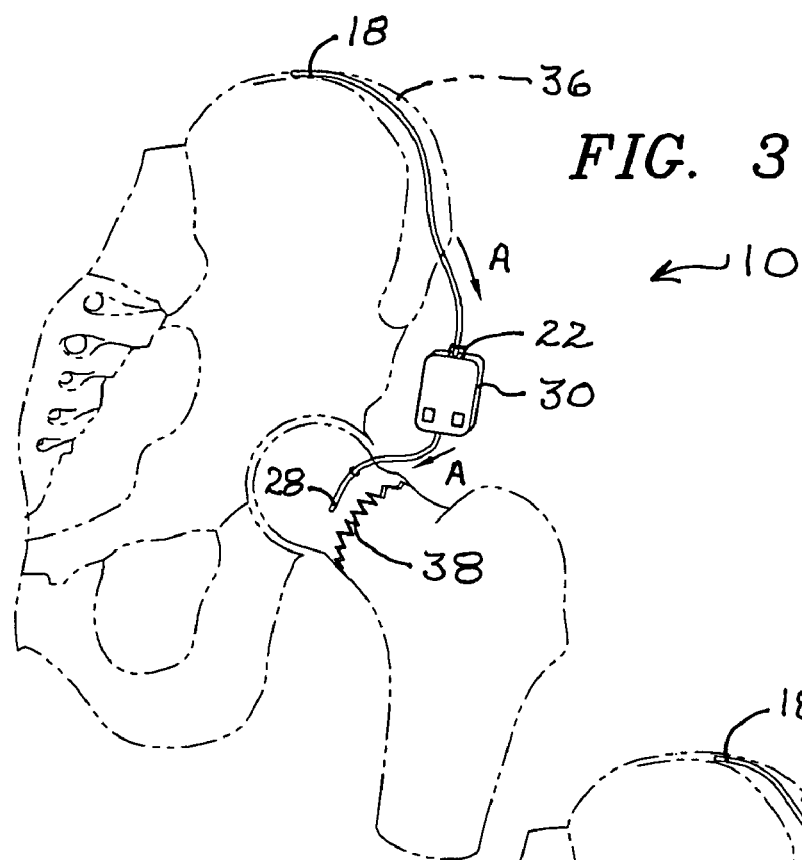
FIG. 3 illustrates placement of a first preferred embodiment of the autologous material delivery apparatus of this invention for treatment of a hip fracture, with portions of the patient's skeleton shown in phantom.

The view of FIG. 3 illustrates use of the autologous material delivery apparatus 10 for treatment of a hip fracture 38. Second delivery end 28 is surgically disposed adjacent hip fracture 38, and first harvest end 18 is surgically disposed within the iliac crest 36.

Figure 4:
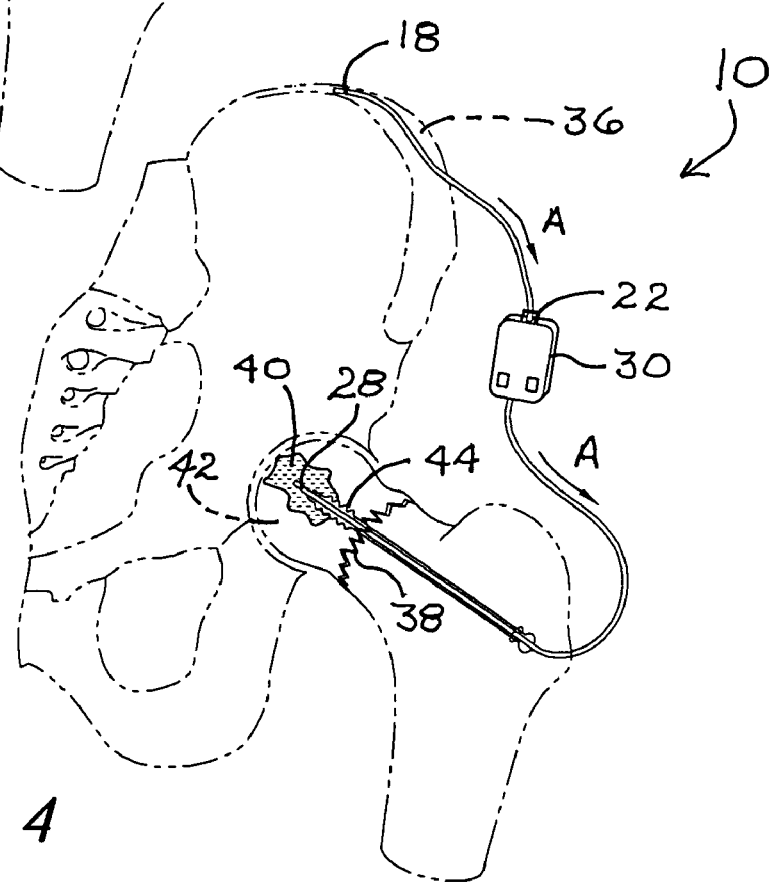
FIG. 4 illustrates placement of a second preferred embodiment of the autologous material delivery apparatus of this invention similar to that of FIG. 3.

The view of FIG. 4 illustrates use of the autologous material delivery apparatus 10 of this invention for treating an area of avascular necrosis 40 of the femoral head 42. In the view of FIG. 4, second delivery end 28 is illustrated as being inside a screw cannulation 44.

The method of this invention comprises selecting an autologous material delivery apparatus 10, surgically implanting first harvest end 18 of harvest catheter 12 in material receiving relation to a predetermined material donor site of the patient, surgically implanting second delivery end of delivery catheter 16 in material delivering relation to a predetermined material delivery site of the patient and activating the pump 14 by the use of flow rate controller 32 and time rate controller 34.

Having thus set forth preferred embodiments for the autologous material delivery apparatus 10 and methods of use for the preferred embodiments, attention is invited to consideration of the following additional features which may be incorporated in apparatus 10 and its use.

As set forth above, a principal utility provided by apparatus 10 of this invention is the delivery of autologous tissue selectively and over time to the desired treatment site. It is intended that pump 14 as well as harvest catheter 12 and delivery catheter 16 may be implanted entirely within the body of a patient. Alternatively, pump 14 and portions of harvest catheter 12 and delivery catheter 16 may actually be disposed external to the patient's body. In the case of total internal placement, operation of pump 14 would be accomplished using known technology such as, for example, radio frequency transmissions or magnetic keys. It is intended that pump 14 would enable medical personnel to monitor and, if necessary, alter the rate or material delivery, the time duration of active material delivery, and even to permit the withdrawing of material samples for appropriate analysis. It is further contemplated that pump 14 might be modified to permit the delivery of additional medicaments through delivery catheter 16, with such medicaments being, for example, antibiotics, additional growth factors, or even markers and dyes.

Thus, while patient treatment using autologous material is certainly old and well known, the apparatus 10 and method of this invention would allow the gradual delivery of treatment material which, it is believed, would not completely deplete the donor site of its desired material. It is also believed that, in addition to the examples given in the above detailed description, apparatus 10 and its attendant method would be applicable to the treatment of delayed unions, nonunions, fresh fractures, bone defect treatment, bone lengthenings, osteomyelitis, and even the management of tumors. If necessary, pump 14 could also be provided with appropriate filter media to allow the passage of only desired, predetermined material to the treatment site. It is also to be understood that pump 14 may be either, for example, mechanical, osmotic, or electrical.

It will thus be seen that the objects set forth above, among those made apparent from the preceding description, are efficiently attained, and, since certain changes may be made in the above constructions and in carrying out the above method without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An autologous material delivery apparatus for providing medical treatment to a patient using treatment material from the patient, said apparatus comprising: a harvest catheter having a first harvest end and a second harvest end, said first harvest end being disposed in material receiving relation to a predetermined material donor site of the patient; a pump having a harvest port and a delivery port in fluid communication with and downstream from said harvest port, said harvest port being operatively connected to said second harvest end of said harvest catheter, whereby the treatment material from the patient's material donor site is configured to enter said pump; and a delivery catheter having a first delivery end and a second delivery end, said first delivery end being operatively connected to said delivery port and said second delivery end being disposed in treatment material delivering relation to a predetermined material treatment site of the patient, whereby the treatment material from the patient's material donor site is delivered to the patient's predetermined material treatment site, said harvest catheter, said pump, and said delivery catheter being disposed within the body of the patient, whereby the material from the material donor site is configured to be delivered to the material treatment site.

2. A method for providing autologous medical treatment to a patient, said method comprising the steps of:
   a. selecting an autologous material delivery apparatus as in claim 1;
   b. surgically implanting said first harvest end in material receiving relation to a predetermined material donor site of the patient;
   c. surgically implanting said second delivery end in material delivering relation to a predetermined material delivery site of the patient; and
   d. Activating the pump.

3. A method for providing autologous medical treatment to a patient as in claim 2 further comprising the step of surgically implanting said harvest catheter, said pump, and said delivery catheter within the patient.

4. A method for providing autologous medical treatment to a patient as in claim 2 further comprising the step of surgically implanting said harvest catheter, said pump, and said delivery catheter within the patient before said activating step.

* * * * *